United States Patent [19]
Hofman et al.

[11] Patent Number: 4,748,991
[45] Date of Patent: Jun. 7, 1988

[54] STICK-LIKE BODY OF COMPACT POWDER

[75] Inventors: Hans J. Hofman; Werner Bruechert, both of Nuernberg; Matthias Hempel, Heroldsberg; Klaus Weber, Rottgau, all of Fed. Rep. of Germany

[73] Assignee: Messrs. Schwan-STABILO Schwanhausser GmbH & Co., Nurnberg, Fed. Rep. of Germany

[21] Appl. No.: 866,227

[22] Filed: May 22, 1986

Related U.S. Application Data

[63] Continuation of Ser. No. 325,493, Nov. 27, 1981, abandoned.

[30] Foreign Application Priority Data

Jan. 30, 1981 [DE] Fed. Rep. of Germany ....... 3103128

[51] Int. Cl.$^4$ ............................................. A45D 40/30
[52] U.S. Cl. ................................................... 132/88.5
[58] Field of Search ........................ 132/89, 88.5, 88.7

[56] References Cited
U.S. PATENT DOCUMENTS 2,623,003 12/1952 Friedlob et al. ..................... 132/89

OTHER PUBLICATIONS

Edward Sagarin—Cosmetics Science & Technology—1957, pp. 223, 225.
M. S. Balsam and Edward Sagarin—Cosmetics, 1972, 2nd Ed., vol. I, pp. 342, 349, and 433.

Primary Examiner—Gregory E. McNeill
Attorney, Agent, or Firm—Louis E. Marn

[57] ABSTRACT

A powder compact material in the form of a stick for cosmetic purposes is made up of powder-like base materials and if necessary additions of binders, lubricants and materials increasing adhesion compacted or bonded together as a body which keeps its form. For stopping the end or outer face of the stick-like body becoming clogged with moisture and sebum on use (so that clean powder compact material would have to be uncovered by cutting, this wasting the material) the compact stick contains as part of the present invention, a particle material, whose particles are harder than the particles of the base materials. The hardness of the particle material may preferably be equal to at least 4.0 on the Mohs' hardness scale. A particle size of 10 to 50 microns and an outer face of the particles which as far as possible is jagged or otherwise rough is responsible for useful effects. Particle materials which may be used are more specially pumice powder, quartz flour, aluminum oxide (corundum) metal carbides, metals and the like, and mixtures thereof. The level of the particle material is more specifically 20 to 40% of the overall weight of the compact material.

14 Claims, 3 Drawing Sheets

STICK-LIKE BODY OF COMPACT POWDER

This is a continuation, of application Ser. No. 06/325,493, filed Nov. 27, 1981, now abandoned.

BACKGROUND OF THE INVENTION

The present invention is with respect to a stick-like body of cosmetic powder compact material designed to keep its form and made up of bonded powder materials with any desired additives in the form of binders, lubricants or materials for increasing adhesion.

Stick-like bodies of powder material of the sort noted on the one hand keep their form to such a degree, and are so strong, that they may be placed loosely in boxes, sleeves or other containers and furthermore may be glued into casings of wood or resin to give a pencil-like structure which may be cut to a point and used in this condition, but on the other hand the consistence of such powder materials is such that the powder may be put on by only lightly touching or brushing them against the skin. Known stick-like powder bodies or refills on these lines (see for example U.S. application Ser. No. 931,072 (of Aug. 4, 1978) which is a CIP of application Ser. No. 721,237 (of Sept. 9, 1976)) are made up of powder-like base materials such as starch, talcum, kaolin, calcium carbonat, powdered mica, which are mixed with the desired coloring pigments in powder form. Dependent on the sort of base materials used, such powder sticks or refills may be compounded with some materials which do not necessarily have to be in powder form, as for example binders, lubricants or materials for increasing adhesion.

Cosmetic refills and other stick-like structures of this sort give the useful effect that the powder may be put on the skin simply by using the stick and without anything like a powder puff. It has however now been seen from experience that a general shortcoming of such stick-like compact powders is that the outer face of the material becomes full of moisture and sebum after a very short time, because such moisture and sebum is in any case present on the skin of the user. For this reason, the outer face of the stick-like structure becomes smooth and more resistant so that no more powder material will be rubbed therefrom even after using it for a generally short time only. While it is true that the stick may be got ready for use again by cutting it to a point so that so far untouched material is uncovered, such an operation is very troublesome for the user, because it is in fact unlikely that she will have any knife-like tool with her; furthermore on cutting back the material to get a clean, new face, there is a great loss of powder material.

GENERAL OUTLINE OF THE INVENTION

For this reason one purpose of the present invention is that of designing a cosmetic stick-like body of the sort noted such that, while having other desired properties as good as in the prior art, as for example the property of readily coating the skin with powder, clogging up and smoothing of the outer face of the body of compact powder is stopped with the outcome that the user no longer has to take the trouble of cutting back to a point the powder material and there is no loss of such material.

For effecting this purpose, and further purposes, the stick-like body of the present invention is characterized by its containing a partical like material in a fine-grain (or finely divided from, the particles being harder than the powder material of the body.

It has been seen, surprisingly, that by the addition of materials which are harder than the powder base materials, there is very much less clogging, or even no clogging, of the outer face of the body and for this reason it gives up powder materials quite as freely. The particle-like material will as a rule be one of the materials making up the body or refill and such material may be said to be neutral, inasmuch as it is not intended to influence the processing of the matterials necessary, the property of the powder of coating the user's skin and the binding properties; in fact it only has the function of stopping smearing and smoothing of the outer face of the powder stick. However it is still possible, within the scope of the invention, for particle-like materials, in the sense the word is used in the present invention, to be used which are such as to have other functions in the powder material as well.

As part of a further development of the invention of good effect, the particle-like material is to have a hardness of at least 4.0 as measured on the Mohs' hardness scale, the hardness being the hardness of the particles themselves. In fact, the powder-like material may be produced by milling a porous or sponge-like solid base material, as for example pumice, which in its lump, unmilled condition has a lower Mohs' hardness, because of its porous structure, while the particles forming the base material are as such harder.

Because the particle material is present in a fine-grain form in the stick-like structure, in which respect it is best for the particle size limit kept to to be within 10 and 110 microns, it does not have any undesired effect on the properties normally desired of such stick-like body or refill. More specially the particle material may have a particle size between 10 and 50 microns. It has been seen from testing that between the particle size of the particle material and its hardness there is a certain correlation inasfar as with an increase in particle size the useful effect desired by the invention may be produced even with a lower hardness.

A further useful effect is produced if the particles of the particle material have an irregularly formed, and more specially, cracked outer face. In fact the particles may for example have a jagged form, or, if they are in a granulated form, they may have a markedly rough outer face. In this respect as well it has been seen that the effect desired in the present invention is more readily produced, the more jagged or rough the outer face of the particles is. In this respect there is again a certain connection or correlation between the hardness and the particle size, inasfar as hardness and/or particle size may be made smaller the more it is possible to make use of particles with ajagged outer form.

Materials keeping to these conditions are for example substances derivated from silicon dioxide such as quartz fluor, aluminum silicate or the pumice powder noted earlier on. It is furthermore possible to make use of mixtures of these materials. Of such materials it is milled pumice which takes the form of jagged particles, whereas quartz flour has somewhat more regularly formed particles or grains, which however are markedly rough.

Because of their specially high hardness, it is furthermore possible, within the scope of the present invention, to make use of aluminum oxides and metal carbides or mixtures thereof. Of the possible forms of aluminum oxide, corundum in a very fine distribution may more specially be used in the are on the market in a great number of different grain sizes and grain size distributions.

Furthermore metal powders may, generally speaking, be used as particle materials, inasfar as the powder particles keep to the conditions named earlier with respect to hardness or aluminum alloys may well be used, in the case of which the desired hardness is produced by the right sort of hardening or treating of the starting material.

The amount at which the particle material is used in the cosmetic stick is not critical. It has been found that, dependent on the hardness, particle size and the form of the outer face, an amount between 20 and 40% by weight is enough.

It has furthermore been found that the effect desired with particular advantage may be produced by using the teaching of the invention in connection with a cosmetic body or stick as noted in U.S. application Ser. No. 931,027. Such a cosmetic compact stick has as its base material powdered mica having a given grain size, or the powder compact stick may be made up of such powder, at least at a level which makes up a great amount of the powder. As binders it is possible to make use, more specially, of water-soluble cellulose derivatives such as methylcellulose, carboxymethylcellulose (CMC), water soluble shellac soap, tragacanth gum, gum arabic, dextrine and other water soluble binders. Furthermore guar gum, a natural hydrocolloid, and derivatives of it may be used.

The mixing of the particle material into the base material for producing the cosmetic powder compact stick of the present invention may be undertaken without any special process steps. It is best for all the powder materials, that is to say together with the particle material to be used in the invention, to be mixed completely so that a homogeneous distribution of all components is made certain of. Following this, the powder mixture so produced is mixed with a water bearing binder and the doughy material so produced is kneaded for the purpose of homogenizing it. The forming of the stick-like powder compact material is best undertaken by extrusion of the compounded material; after this there is an operation for drying off water and in this way a stick-like body, which keeps its form, is produced. The amounts of water used in addition will be dependent on the sort of water soluble binder used and will be known by one trained in the art so that no very detailed account is necessary here on this point.

The table now to be presented gives four examples of preferred compositions of a cosmetic stick material of the present invention. The examples are numbered 1 to 4 in the columns of the table. The table gives not only the percentage compositions (percentages by weight) but furthermore the parts of the various components added in each case. The particle size of the particle material used in each case is mainly between 30 and 40 microns, All four compositions go to make it clear that undesired smearing and clogging of the outer face of the powder compact material may be stopped.

TABLE

| Components | Number 1 % | Number 1 parts | Number 2 % | Number 2 parts | Number 3 % | Number 3 parts | Number 4 % | Number 4 parts |
| --- | --- | --- | --- | --- | --- | --- | --- | --- |
| Base material (filler): | | | | | | | | |
| talcum | 22 | 60.0 | 25 | 60.0 | 30 | 50.0 | 20 | 45.0 |
| kaolin | | | | | 6 | 10.0 | | |
| mica | 30 | 80.0 | 35 | 80.0 | | | | |
| particle material: | | | | | | | | |
| pumice powder | 20 | 60.0 | | | | | | |
| quartz flour | | | 20 | 50.0 | 30 | 50.0 | | |
| aluminum oxide | | | | | | | 30 | 60.0 |
| lubricants: | | | | | | | | |
| Zn stearate | | | | | 8 | 11.0 | | |
| Mg stearate | 4 | 10.0 | | | | | | |
| Ca stearate | | | | | | | 6 | 15.0 |
| materials for increasing adhesion: | | | | | | | | |
| bentonite | 1 | 1.0 | 1 | 1.0 | | | | |
| Mg myristate | 4 | 10.0 | 4 | 10.0 | | | | |
| Mg—Al—silicagel | | | | | 6 | 10.0 | | |
| binders: | | | | | | | | |
| CMC | | | | | | | 2 | 4.0 |
| guar gum | 2 | 5.0 | | | | | | |
| high viscosity polyvinylpyrrolidone (PVP) | | | | | 3 | 5.0 | | |
| pigments: | | | | | | | | |
| coloring pigments | 12 | 30.0 | 5 | 10.0 | 14 | 20.0 | | |
| nacreous pigments | | | 10 | 30.0 | | | 42 | 90.0 |
| white pigments | 5 | 10.0 | | | 3 | 4.0 | | |
| Percentages | 100 | | 100 | | 100 | | 100 | |

DETAILED ACCOUNT OF THE INVENTION USING THE FIGURES

Further details of the invention will be seen from the account now to be given using the figures.

Figures 1A, 1B:
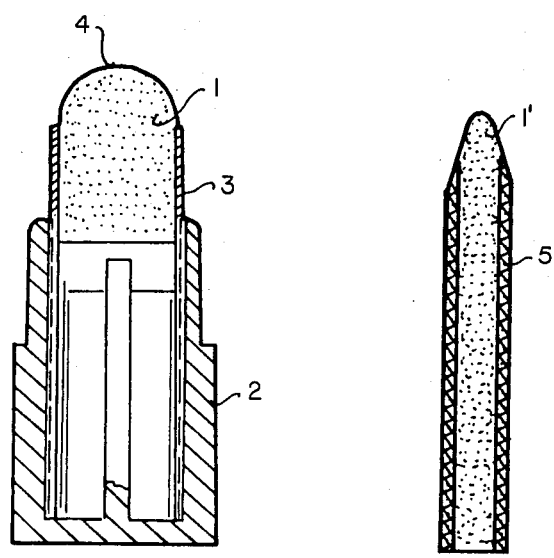
FIGS. 1a, 1b are diagrammatic views of two known forms of powder sticks in lengthways section, the powder stick or refill being compounded on the lines of the present invention.

In FIG. 1a the reader will see a powder stick unit with a powder stick 1, in the narrow sense of the word, or refill and a casing 2 of metal or molded resin. A screw sleeve 3 is placed within casing 2 so that by turning the screw sleeve 3 in relation to casing 2 the powder compact stick 1 may be screwed outwards and the user will be able to put the front end 4 or face of the powder stick on her skin for coating it. with powder.

In FIG. 1b a powder stick unit will be seen whose powder stick 1' is taken up in a stem or casing 5 of wood or molded resin so that after the uncovered pointed end of the powder body has been used up the casing may be cut back uncovering In their general looks the powder stick units of FIGS. 1a and 1b are not different to known cosmetic powder units.

Figure 2:
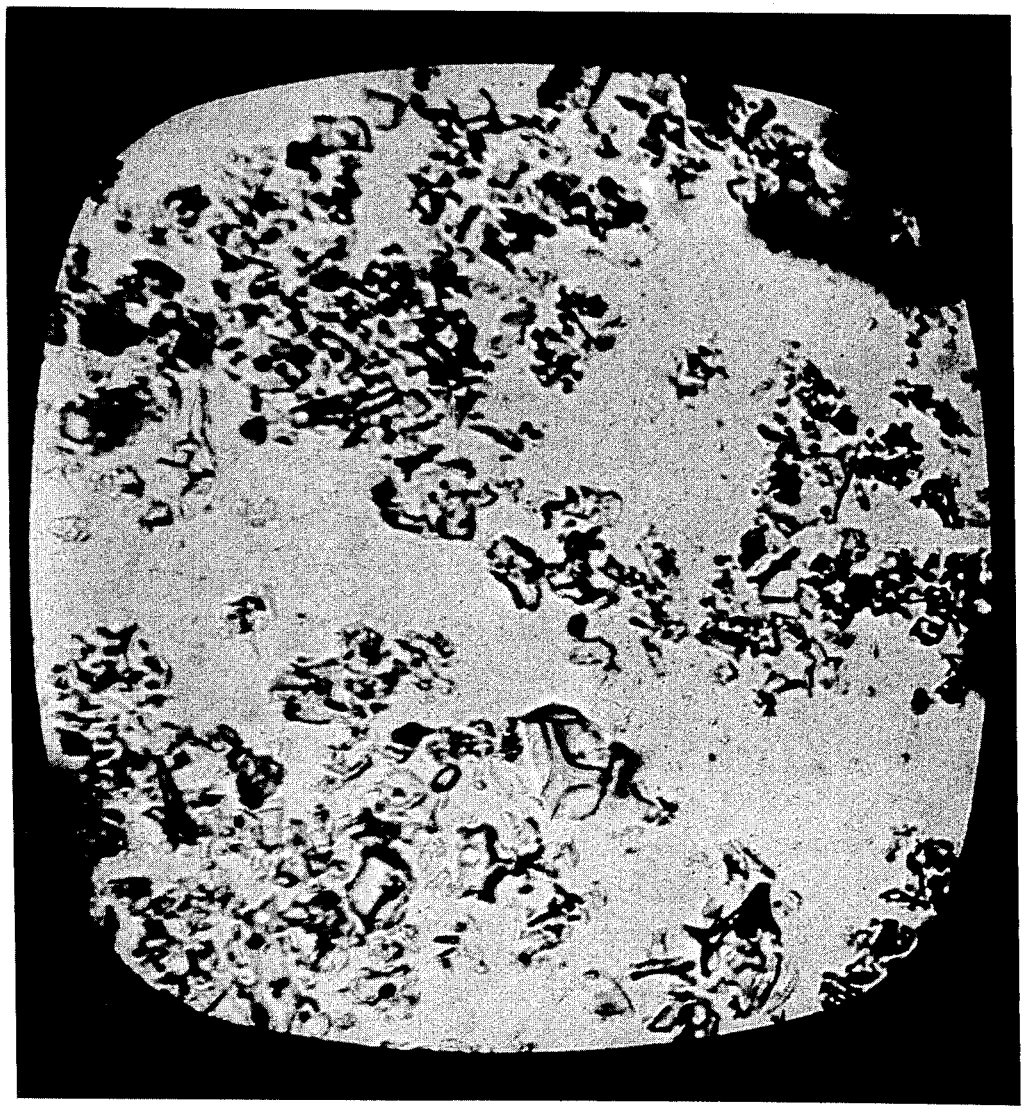
FIGS. 2 and 3 are microphotographs (magnification: 450) of particle materials which may be used in the present invention, that is to say pumice powder and in the other case quartz flour.
Figure 3:
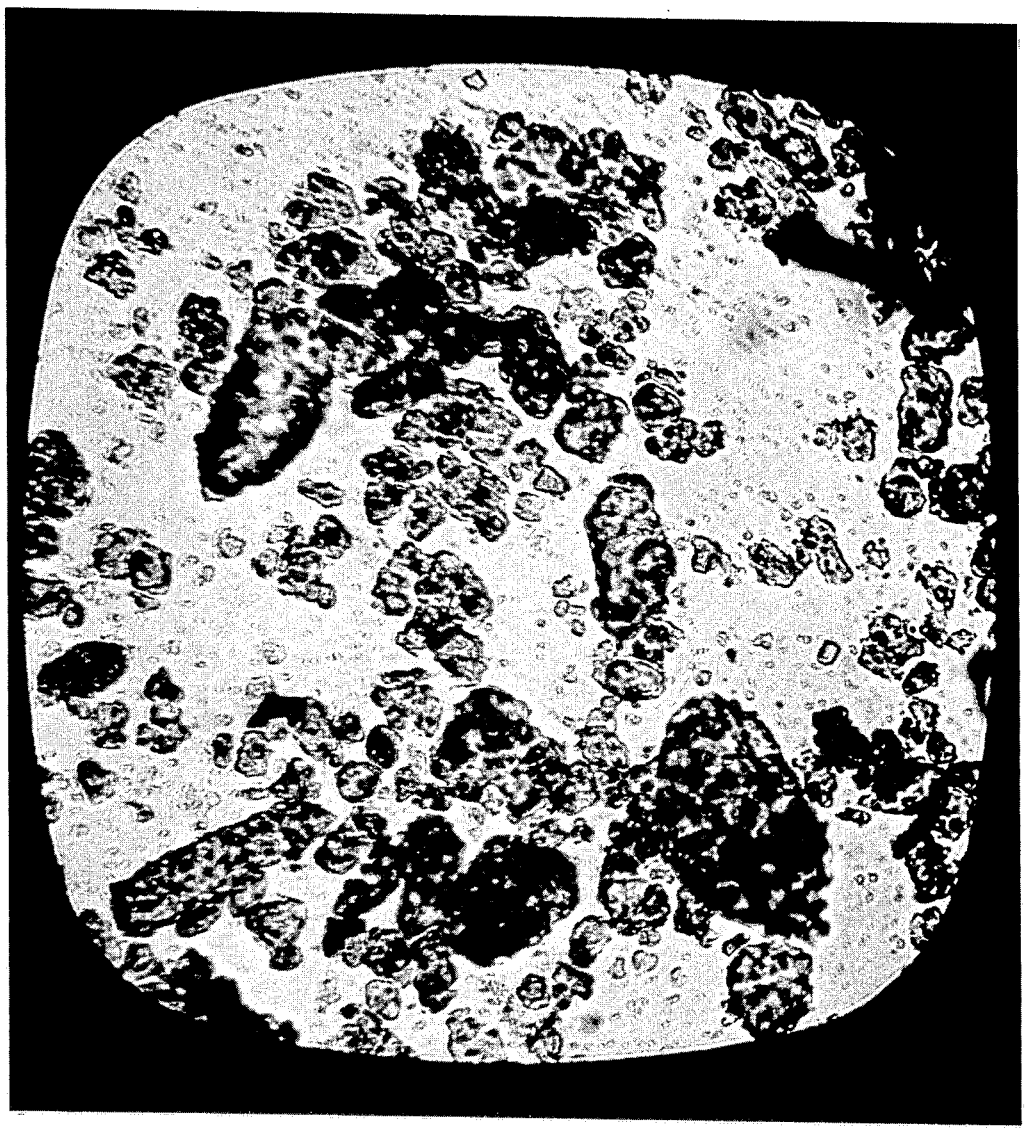

In FIGS. 2 and 3, with a magnification of 450, the particle material will be seen. The pumice powder to be seen in FIG. 2 has a markedly jagged form, that is to say with a very irregular and cracked outline. The average size of the pumice particles is about 30 to 50 microns.

The quartz flour particles to be seen in FIG. 3 will be seen to have a granulated form. It is clearly possible to see the roughness average size of particles is in this case about 40 to 60 microns.

We claim:

1. An improved cosmetic, which comprises:
a stick-like compact powder body in compressed form for applying powder to skin of a user by brusing a contact face of said compact powder body directly against said skin of said user, said compact powder body comprised of one or more base materials selected from the group consisting of starch, talcum, kaolin, calcium carbonate and ica, pigments, lubricants and said compact powder body, said improved compact powder body a particulate material distinct from any of said base materials and selected from the groups consisting of silica, silca derivatives, aluminum oxides and mixtures thereof, said particulate material having an irregular form and a rough surface and of a particle size of between 10 and 100 microns and a hardness in excess of the hardness of any of said base materials of said compact powder body whereby brushing of said compact powder body against said skin of said user prevents clogging of said contact face of said compact powder body with moisture and sebum thereof.

2. The improved cosmetic stick-like compact powder body as defined in claim 1 wherein said particulate material is of a particle size of from 30 to 40 microns.

3. The improved cosmetic stick-like compact powder body as defined in claim 1 wherein said particulate materials is present in an amount of up to about 40% by weight.

4. The improved cosmetic stick-like compact powder body as defined in claim 1 wherein the particulate material is present in an amount of from 20% to 30% by weight.

5. The improved cosmetic stick-like compact powder body as defined in claim 1 wherein said particulate material is of a hardness of at least 4.0 on the MOHS hardness scale.

6. The improved cosmetic stick-like compact powder body as defined in claim 1 wherein said particulate material is quartz flour.

7. The improved cosmetic stick-like compact powder body as defined in claim 1 wherein said particulate material is aluminum silicate.

8. An improved cosmetic, which comprises:
a stick-like comapct powder body in compressed form for applying powder to skin of a user by brushing a contact face of said compact powder body directly against said skin of said user, said compact powder body comprised of one or more base materials selected from the group consisting of starch, talcum, kaolin, calcium carbonate and mica, pigments, lubricants and a particulate material distinct from any of said base materials and selected from the group consisting of silica, silica derivatives, aluminum oxides and mixtures thereof, said particulate material having an irregular and jagged form and a cracked surface and of a particle size of between 10 and 100 microns and a hardnes in excess of the hardness of any of said base materials of said compact powder body whereby brushing of said compact powder body against said skin of said user prevents clogging of said contact face of said compact powder body with moisture and sebum thereof.

9. The improved cosmetic stick-like compact powder body as defined in claim 8 wherein said particulate material is present in an amount of up to about 40% by weight.

10. The improved cosmetic stick-like compact powder body as defined in claim 8 wherein the particulate material is present in an amount of from 20% to 30% by weight.

11. The improved cosmetic stick-like compact powder body as defined in claim 8 wherein said particulate material is of a hardness of at least 4.0 on the MOHS hardness scale.

12. The improved cosmetic stick-like compact powder body as defined in claim 8 wherein said particulate material is quartz flour.

13. The improved cosmetic stick-like compact powder body as defined in claim 8 wherein said particulate material is pumice powder.

14. The improved cosmetic stick-like compact powder body as defined in claim 13 wherein said pumice powder is obtained by milling solid pumice.

* * * * *